United States Patent [19]

Horváth et al.

[11] Patent Number: 4,537,899

[45] Date of Patent: Aug. 27, 1985

[54] ANTIVIRAL ACYLATED 1,2,4-TRIAZOLE DERIVATIVES

[75] Inventors: István Horváth; Tibor Láng; László Pongo; József Reiter; Tamás Somorai; Géza Szilágyi; Lajos Toldy, all of Budapest, Hungary

[73] Assignee: BIOGAL Gyógyszergyár, Debrecen, Hungary

[21] Appl. No.: 526,694

[22] Filed: Aug. 25, 1983

[30] Foreign Application Priority Data

Sep. 1, 1982 [HU] Hungary ............................... 2797/82

[51] Int. Cl.³ ..................... A01N 43/64; A61K 31/41; C07D 249/14
[52] U.S. Cl. ..................................... 514/384; 548/265
[58] Field of Search .......................... 548/265; 424/269

[56] References Cited
FOREIGN PATENT DOCUMENTS 113362  6/1975  German Democratic Rep. ..................................... 548/265
2084140  4/1982  United Kingdom ................ 548/265

OTHER PUBLICATIONS

Blank et al., J. Med. Chem., vol. 16, pp. 694–696, (1972).
Coburn et al., Chem. Abstracts, vol. 74, Abstract No. 22770f, (1971).

Primary Examiner—Alton D. Rollins
Attorney, Agent, or Firm—Keil & Weinkauf

[57] ABSTRACT

The invention relates to acylated 1,2,4-triazole derivatives of general formula I

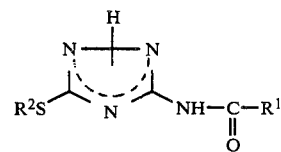

wherein
$R^1$ represents an unsubstituted phenyl group or a phenyl group substituted by one or more halogen atoms, lower alkyl, alkoxy, acyloxy, hydroxy, amino, azido, nitro, trifluoromethyl, lower alkylthio, alkylsulfinyl, or alkylsulfonyl group, and
$R^2$ stands for a $C_{1-6}$ alkyl group or a phenyl lower alkyl group which is either unsubstituted or substituted in the aromatic nucleus by a halogen atom or a nitro group, and their pharmaceutically acceptable salts, and a process for preparing them. The new compounds according to the invention exhibit valuable antiviral activity.

6 Claims, No Drawings

ANTIVIRAL ACYLATED 1,2,4-TRIAZOLE DERIVATIVES

The invention relates to novel acylated 1,2,4-triazole derivatives of general formula I

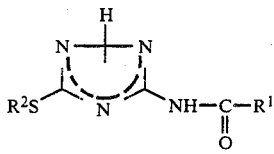

wherein
$R^1$ represents an unsubstituted phenyl group or a phenyl group substituted by one or more halogen atoms, lower alkyl, alkoxy, acyloxy, hydroxy, amino, azido, nitro, trifluoromethyl, lower alkylthio, alkylsulfinyl, or alkylsulfonyl group, and
$R^2$ stands for a $C_{1-6}$ alkyl group or a phenyl lower alkyl group which is either unsubstituted or substituted in the aromatic nucleus by a halogen atom or a nitro group,
and their pharmaceutically acceptable salts, furthermore to a process for the preparation thereof.

The invention relates to all possible tautomeric forms of the compounds of general formula I, as well as to their mixtures, too.

The compounds covered by general formula I are new.

The invention provides a process for the preparation of compounds of general formula I, wherein $R^1$ and $R^2$ have the same meaning as above, wherein:

(a) a compound of general formula II—

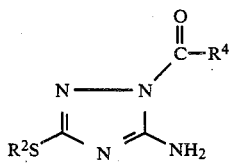

wherein
$R^1$ and $R^2$ have the same meaning as above—is submitted to thermal rearrangement either by melting or by heating it in an inert solvent, or (b) a mixture of a compound of general formula III—

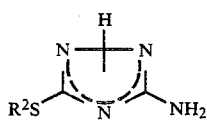

wherein
$R^2$ has the same meaning as above—and an inert solvent is brought to reaction in the presence of an organic acid binding agent at 150° to 220° C. with a compound of general formula IV,

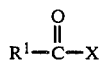

wherein $R^1$ has the same meaning as above and X stands for a halogen atom, and the resulting product is optionally converted by a pharmaceutically acceptable acid into an acid addition salt.

According to a preferred process of the invention [Method (a)] a compound of general formula II—wherein $R^1$ and $R^2$ have the same meaning as above—is melted at a temperature set between its melting point and 260° C., preferably at a temperature higher by 10° to 20° C. than its melting point, for 10 to 300 minutes, preferably for 10 to 60 minutes, or is heated for 30 to 300 minutes, preferably for 30 to 90 minutes in some inert solvent, preferably in sulfolane, dimethylformamide, or dimethylsulfoxide, then the resulting compound of general formula I—wherein $R^1$ and $R^2$ have the same meaning as above—is isolated by a procedure known per se.

According to a further preferred process of the invention [Method (b)] a mixture of a compound of general formula III—wherein $R^2$ has the same meaning as above—and an inert solvent, preferably sulfolane, dimethylformamide, dimethylsulfoxide, chlorobenzene or anisole, is made to react in the presence of an organic acid binding agent, preferably gamma-picoline, at a temperature ranging from 120° to 220° C., preferably at 160° to 180° C., with a compound of general formula IV—wherein $R^1$ has the same meaning as above and X stands for a chlorine atom, then the resulting compound of general formula I—wherein $R^1$ and $R^2$ have the same meaning as above—is isolated by a method known per se.

The starting materials of general formula II, applied for the preparation of compounds of general formula I of the invention, are also new. Solely 1-(4-methoxy-benzoyl)-3-methylthio-5-amino-1H-1,2,4-triazole (East German Pat. No. 113,362) is known from the literature.

According to a preferred process of the invention compounds of general formula II can be prepared by adding to a solution of 1M of a compound of general formula III—where $R^2$ has the same meaning as above—in an organic aprotic solvent, in the presence of 1 to 1.8M of an organic base, preferably pyridine, dimethylamine or gamma-picoline—optionally in the presence of 4-dimethylamino-pyridine, an acylating catalyst—at a temperature of −50° C. to +150° C., 1 to 1.8M, preferably 1 to 1.2M of a compound of general formula IV, where $R^1$ has the same meaning as above and X represents a halogen atom. Following the concluded reaction the resulting products of general formula II—where $R^1$ and $R^2$ have the same meaning as above—are isolated according to a procedure known per se.

Compounds of general formula II can also be prepared by carrying out the reaction between 1M of a compound of general formula III—where $R^2$ has the same meaning as above—and 1 to 1.8M, preferably 1 to 1.2M, of a compound of general formula IV—wherein $R^1$ has the same meaning as above and X stands for a halogen atom—in an inert solvent, preferably benzene or toluene, applying potassium carbonate as acid binding agent and polyethyleneglycol as acylating catalyst preferably in an amount of 1 to 5 percent, at the boiling point of the solvent.

Compounds of general formula III—wherein $R^2$ has the same meaning as above—are mostly known from the literature and can be prepared by methods known per se [Chem. Ber. 54, 2089 (1921); Arch. Pharm. 308, 189 (1925); J. Chem. Soc. 1961, 5137].

Compounds of general formula IV are known. In the process of the invention the use of acylchlorides is preferred.

In the course of the testing of compounds of general formula I of the invention it was found that they possess valuable therapeutic properties, namely antiviral activity, while exhibiting low toxicity. Oral $LD_{50}$ amounts to 3200 mg/kg in the case of 3-methylthio-5-(2-methyl-benzoyl-amino)-1H-1,2,4-triazole, in rats.

The antiviral potency of the compounds covered by the invention is demonstrated on the following representative compounds:

3-methylthio-5-(2-methyl-benzoyl-amino)-1H-1,2,4-triazole (Example 47),
3-methylthio-5-(2-bromo-benzoyl-amino)-1H-1,2,4-triazole (Example 53),
3-methylthio-5-(2-nitro-benzoyl-amino)-1H-1,2,4-triazole (Example 61),
3-methylthio-5-(2-chloro-benzoyl-amino)-1H-1,2,4-triazole (Example 63),
3-methylthio-5-(2-methylthio-benzoyl-amino)-1H-1,2,4-triazole (Example 70), and
3-ethylthio-5-(2-methyl-benzoyl-amino)-1H-1,2,4-triazole (Example 73).

The antiviral testing of the compounds was carried out in two steps. First the dose-response curve of cytotoxicity was plotted, then the antiviral activity was assayed in cell cultures containing nontoxic amounts of the compound.

1. The cytotoxicity of the compounds was assayed in HeLa and RK-13 cell cultures by quantitating the protein content of the cells [S. Horváth: Cytotoxicity of drugs and diverse chemical agents to cell cultures, Toxicology, 16, 59 (1980)]. From the data of the dose-response curve the 50 percent cytotoxic concentration of the compounds was determined ($CT_{50}$), i.e. the concentration inhibiting cell proliferation by 50 percent. Similarly from the data of the dose-response curve the highest concentration of the compounds where cell proliferation compared to the control is not inhibited at all, can be determined, too (0 percent cytotoxic concentration, $CT_0$). To simplify matters, in the Table the logarithm of these values is summarized (i.e. log $CT_0 = 1$ representing a concentration of 10 μg/ml).

TABLE 1

| Example No. | Cytotoxicity (log μg/ml) | | | |
|---|---|---|---|---|
| | HeLa | | RK 13 | |
| | $CT_{50}$ | $CT_0$ | $CT_{50}$ | $CT_0$ |
| 47 | 2.0 | 1.6 | 1.9 | 1.1 |
| 53 | 2.1 | 1.6 | 1.9 | 1.4 |
| 61 | 1.6 | 1.0 | 1.8 | 1.2 |
| 63 | 1.7 | 0.9 | 1.9 | 1.2 |
| 70 | 1.9 | 1.3 | 1.7 | 1.2 |
| 73 | 1.7 | 0.9 | | |

2. Testing of antiviral potency: a compound is an antiviral agent if it is able to inhibit significantly virus proliferation at 0 percent cytotoxic concentration ($CT_0$). The rate of antiviral activity is expressed by the reduction of virus titers ($TCID_{50}$) in relation to the control. If the reduction amounts to several orders of magnitude, the ratio of $TCID_{50}$ values can represent several logarithm units. This should be around 6 in case of a potent antiviral agent. In the antiviral testing the following virus strains were used: Herpes simplex virus type 1, Adenovirus type 5, Rubeola virus (strain Judith) and Influenza virus AO (PR8). For the assay of the Herpes virus HeLa, of the Adenovirus Hep-2 and for the Rubeola virus RK-13 cell cultures were used. The infectivity of Influenza virus was measured by the rolling drum type method containing chorioallantois membranes [S. Horváth: A New and Sensitive Method of the Rolling Drum Type for Influenza Virus Titration. Acta Microbiol. Acad. Sci. Hung. 1, 481 (1954)].

In the assay of viruses tenfold serial dilutions were used for the inoculation of four parallel cell cultures for each. The nutritive medium contained the $CT_0$ concentrations of the test compounds. Following a suitable incubation period $TCID_{50}$ values were calculated according to Reed-Muench [L. J. Reed and H. Muench: American J. Hyg. 27, 493 (1938)] on the basis of the cytotoxic effect of the viruses. The rate of antiviral activity was expressed by the difference of the logarithms of the $TCID_{50}$ titers of the control and the test compound, resp.

Table 2 clearly demonstrates that the above compounds exhibit at concentrations of $CT_0$ highly significant antiviral activity against Rubeola virus, as there is a difference between the log $TCID_{50}$ values of the control and the test compound of 5–7 logarithm units except for Example 61.

With antiviral substances known from the literature this amounts only to 3 to 4 logarithm units (there is no compound which would only be effective against Rubeola virus).

TABLE 2

| Antiviral effect against Rubeola virus at concentrations of $CT_0$ | |
|---|---|
| Example No. | Δlog $TCID_{50}$ |
| 47 | ≧6.8 |
| 53 | ≧6.8 |
| 61 | 3.0 |
| 63 | ≧5.3 |
| 70 | ≧5.3 |
| 73 | ≧6.0 |

The following examples illustrate but do not limit the scope of invention.

Compounds of general formula II applied in the invention are prepared according to the following procedure:

EXAMPLE 1

1-(4-Chloro-benzoyl)-3-methylthio-5-amino-1,2,4-triazole 4.7 g of pyridine are added to a solution of 7.8 g of 3-methylthio-5-amino-1H-1,2,4-triazole [Monatshefte für Chemie 106, 1291 (1975)] in 200 ml of dioxane, then 10.8 g of 4-chloro-benzoylchloride are added dropwise at −5° C. The reaction mixture is stirred for one hour at −5° C., then for a further one hour at room temperature, finally 100 ml of water are added at water-cooling and the entire mixture is extracted with chloroform. The chloroform layer is washed with water, dried, evaporated to dryness, yielding 13.46 g (83.5 percent) of 1-(4-chloro-benzoyl)-3-methylthio-5-amino-1,2,4-triazole, m.p. 175° to 177° C. (following boiling with alcohol).

Further compounds of general formula II prepared according to the above procedure are listed in Table 3.

TABLE 3

| Example No. | 1-(X—Benzoyl)-5-Y—thio-5-amino-1,2,4-triazole | | M.p. °C. |
|---|---|---|---|
| | X | Y | |
| 2 | 2-Chloro | Methyl | 164–166 |
| 3 | H | Methyl | 150–152 |
| 4 | 2-Acetoxy | Methyl | 138–140 |
| 5 | 2-Carbomethoxy | Methyl | 207–210 |
| 6 | 3,4-Dimethoxy | Methyl | 175–176 |
| 7 | 3,4,5-Trimethoxy | Methyl | 154–156 |
| 8 | H | Benzyl | 135–137 |
| 9 | 3-Chloro | Methyl | 157–158 |
| 10 | 2-Fluoro | Methyl | 157–159 |
| 11 | 2-Iodo | Methyl | 160–161 |
| 12 | 4-Iodo | Methyl | 187–189 |
| 13 | 3-Trifluoromethyl | Methyl | 157–158 |
| 14 | 2,6-Dichloro | Methyl | 201–203 |
| 15 | 2,4-Dichloro | Methyl | 181–182 |
| 16 | 2,5-Dichloro | Methyl | 175–177 |
| 17 | 2,5-Dimethyl | Methyl | |
| 18 | 2-Methoxy | Methyl | 145–148 |
| 19 | 2-Nitro | Methyl | 226–229 |
| 20 | 4-Nitro | Methyl | 220–221 |
| 21 | 2-Chloro | Butyl | 111–112 |
| 22 | 2-Chloro | 4-Nitro-benzyl | 168–170 |
| 23 | 2-Azido | Methyl | 156–158 |
| 24 | 4-Azido | Methyl | 183–185 |
| 25 | 2-Chloro | Benzyl | 147–149 |
| 26 | 3-Methyl | Methyl | 155–157 |
| 27 | 4-Methyl | Methyl | 186–188 |
| 28 | 2-Methylthio | Methyl | 175–178 |
| 29 | 4-Bromo | Methyl | 180–182 |
| 30 | 2-Methyl | Ethyl | 87–90 |
| 31 | 2-Methylsulfonyl | Methyl | |
| 32 | 2-Methylsulfonyl | Methyl | |
| 33 | 2-Bromo | Ethyl | |
| 34 | 2-Chloro | Ethyl | |
| 35 | 2-Fluoro | Ethyl | |
| 36 | 2-Nitro | Ethyl | |
| 37 | 2-Iodo | Ethyl | |
| 38 | 2-Methylthio | Ethyl | |
| 39 | 2-Bromo | Propyl | |
| 40 | 2-Chloro | Propyl | |
| 41 | 2-Fluoro | Propyl | |
| 42 | 2-Iodo | Propyl | |
| 43 | 2-Nitro | Propyl | |
| 44 | 2-Methyl | Propyl | |
| 45 | 2-Methylthio | Propyl | |

EXAMPLE 46

1-(2-Methyl-benzoyl)-3-methylthio-5-amino-1,2,4-triazole

Method A

A solution of 31.2 g (0.2M) of 2-methyl-benzoylchloride in 50 ml of dioxane is added dropwise during 30 minutes to a mixture of 17.5 g (0.14M) of 3-methylthio-5-amino-1H-1,2,4-triazole, 14 g (0.18M) of pyridine and 150 ml of dioxane at constant stirring and temperature of 0° to 5° C. The reaction mixture is stirred for 30 minutes at this temperature, then for 4 hours at room temperature and is finally poured into 600 ml of water. The precipitate formed is filtered, washed with water and dried. Yield: 32.8 g (98 percent), m.p. 154° to 156° C. (recrystallized from alcohol).

Method B

A solution of 31.2 g (0.2M) of 2-methyl-benzoylchloride in 50 ml of dioxane is added dropwise during 30 minutes to a mixture of 22.6 g (0.174M) of 3-methylthio-5-amino-1H-1,2,4-triazole, 14.5 g (0.19M) of pyridine and 150 ml of dioxane at constant stirring and 100° C. The reaction mixture is worked up according to the procedure described under Method A. Yield: 42.3 g (98 percent), m.p. 155° to 156° C. (recrystallized from alcohol).

Method C

A solution of 1.55 g (10 mmole) of 2-methyl-benzoylchloride in 5 ml of dioxane is added dropwise during 30 minutes to a mixture of 1.3 g (10 mmole) of 3-methylthio-5-amino-1H-1,2,4-triazole, 10 ml of dioxane, 0.88 g (11 mmole) of pyridine and 50 mg of 4-dimethylamino-pyridine at constant stirring. The reaction mixture is stirred for further 2 hours at room temperature. The mixture is worked up according to the procedure described under Method A. Yield: 1.6 g (67 percent).

Method D

A solution of 1.55 g (10 mmole) of 2-methyl-benzoylchloride in 5 ml of dioxane is added dropwise during 30 minutes to a mixture of 1.3 g (10 mmole) of 3-methylthio-5-amino-1H-1,2,4-triazole, 1.45 g (10.5 mmole) of potassium carbonate, 26 ml of benzene and 50 mg of polyethyleneglycol at constant stirring, and the reaction mixture is heated under reflux for 2 hours. The solvent is evaporated, the residue worked up with water, the crystals are filtered and recrystallized from alcohol. Yield: 1.7 g (71 percent).

Compounds of general formula I are prepared according to the following examples:

EXAMPLE 47

3-Methylthio-5-(2-methyl-benzoyl-amino)-1H-1,2,4-triazole

Method A 20 g of 1-(2-methyl-benzoyl)-3-methylthio-5-amino-1,2,4-triazole (prepared according to either procedure A or B of Example 46) is heated for 60 minutes to 240° C. The molten compound is ground up to a powder. Yield: 18.8 g (94 percent), m.p. 208° to 209° C. (recrystallized from alcohol).

Further compounds prepared according to Method A in Example 47 are summarized in Table 4.

TABLE 4

| Example No. | 3-Y—Thio-5-(X—benzoyl-amino)-1H—1,2,4-triazole | | M.p. °C. |
|---|---|---|---|
| | Y | X | |
| 48 | Methyl | 4-Chloro | 264–266 |
| 49 | Methyl | H | 229–231 |
| 50 | Methyl | 3,4-Dimethoxy | 219–221 |
| 51 | Methyl | 3-Chloro | 229–230 |
| 52 | Methyl | 2-Fluoro | 207–209 |
| 53 | Methyl | 2-Bromo | 204–206 |
| 54 | Methyl | 3-Trifluoromethyl | 230–231 |
| 55 | Methyl | 4-Iodo | 290–293 |
| 56 | Methyl | 2-Iodo | 201–204 |
| 57 | Methyl | 2,4-Dichloro | 227–229 |
| 58 | Methyl | 2,5-Dichloro | 252–254 |
| 59 | Methyl | 2,6-Dichloro | 269–271 |
| 60 | Methyl | 2-Methoxy | 206–208 |
| 61 | Methyl | 2-Nitro | 259–262 |
| 62 | Methyl | 4-Nitro | 283–285 |
| 63 | Methyl | 2-Chloro | 214–215 |
| 64 | Butyl | 2-Chloro | 148–150 |
| 65 | 4-Nitro-benzyl | 2-Chloro | 266–269 |
| 66 | Benzyl | 2-Chloro | 196–197 |
| 67 | Methyl | 2,5-Dimethyl | |

TABLE 4-continued

| Example No. | 3-Y—Thio-5-(X—benzoyl-amino)-1H—1,2,4-triazole Y | X | M.p. °C. |
|---|---|---|---|
| 68 | Methyl | 3-Methyl | 193–195 |
| 69 | Methyl | 4-Methyl | 263–265 |
| 70 | Methyl | 2-Methylthio | 248–250 |
| 71 | Methyl | 4-Bromo | 268–270 |
| 72 | Methyl | 2-Amino | 190–191 |
| 73 | Ethyl | 2-Methyl | 156–158 |
| 74 | Methyl | 2-Methylsulfonyl | |
| 75 | Methyl | 2-Methylsulfonyl | |
| 76 | Ethyl | 2-Bromo | |
| 77 | Ethyl | 2-Chloro | |
| 78 | Ethyl | 2-Fluoro | |
| 79 | Ethyl | 2-Nitro | |
| 80 | Ethyl | 2-Iodo | |
| 81 | Ethyl | 2-Methylthio | |
| 82 | Propyl | 2-Bromo | |
| 83 | Propyl | 2-Chloro | |
| 84 | Propyl | 2-Fluoro | |
| 85 | Propyl | 2-Iodo | |
| 86 | Propyl | 2-Nitro | |
| 87 | Propyl | 2-Methyl | |
| 88 | Propyl | 2-Methylthio | |

Method B 15 g of 1-(2-methyl-benzoyl)-3-methylthio-5-amino-1,2,4-triazole (prepared either according to Method A or B of Example 46) in 15 ml of sulfolane are heated for 60 minutes to 240° C., then poured into 60 ml of water. The precipitate is filtered, washed with water and dried. Yield: 14.5 g (96.5 percent), m.p. 209° to 210° C. (alcohol).

Method C

A mixture of 1.3 g (10 mmole) of 3-methylthio-5-amino-1H-1,2,4-triazole, 4 ml of sulfolane, 1.02 g (11 mmole) of gamma-picoline and 1.8 g (11.5 mmole) of 2-methyl-benzoylchloride is heated first to 145° C. for 60 minutes, and then to 170° C. for a further 60 minutes. The mixture is left to cool off, then it is thoroughly mixed with water. The precipitate formed is filtered, washed with water and dried. Yield: 2.3 g (96 percent), m.p. 208° to 210° C.

EXAMPLE 89

3-Methylthio-5-(2-hydroxy-benzoyl-amino)-1H-1,2,4-triazole 0.5 g of 1-(2-acetoxy-benzoyl)-3-methylthio-5-amino-1,2,4-triazole, prepared according to the procedure described in Example 4, is heated without solvent to 220° to 230° C. in an oil bath for 30 minutes. Following cooling the solidified melt is heated with alcohol, yielding 0.15 g (35 percent) of 3-methylthio-5-(2-hydroxy-benzoyl-amino)-1H-1,2,4-triazole, m.p. 306° to 309° C.

What we claim is:

1. Acylated 1,2,4-triazole derivatives of formula I

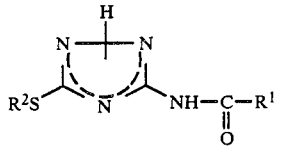

wherein
R$^1$ represents an unsubstituted phenyl group or a phenyl group substituted by one or more halogen atoms, lower alkyl, lower alkoxy, acyloxy, carbomethoxy hydroxy, amino, azido, nitro, trifluoromethyl, lower alkylthio, lower alkylsulfinyl, or lower alkylsulfonyl group, and
R$^2$ stands for a C$_{1-6}$ alkyl group or a phenyl lower alkyl group which is either unsubstituted or substituted in the aromatic nucleus by a halogen atom or a nitro group,
and their pharmaceutically acceptable salts.

2. A compound of the formula I of claim 1, wherein R$^1$ is unsubstituted phenyl and R$^2$ is methyl or ethyl.

3. A compound of the formula I of claim 1, wherein R$^1$ is phenyl substituted by methyl, bromo, chloro or nitro, and R$^2$ is methyl or ethyl.

4. A compound of the formula I of claim 1, which is 3-methylthio-5-(2-methyl-benzoyl-amino)-1H-1,2,4-triazole.

5. A compound of the formula I of claim 1, which is 3-methylthio-5-(2-bromo-benzoyl-amino)-1H-1,2,4-triazole.

6. Antiviral pharmaceutical compositions containing as active ingredient an effective amount of one or more compounds of formula I—wherein R$^1$ and R$^2$ have a meaning as claimed in claim 1—or a pharmaceutically acceptable salt thereof, and a conventional inert, non-toxic, solid or liquid carrier and/or additive.

* * * * *